United States Patent
Jass

(10) Patent No.: US 7,247,744 B2
(45) Date of Patent: Jul. 24, 2007

(54) PROCESS FOR THE PREPARATION OF PROBUCOL DERIVATIVES

(75) Inventor: Paul Alan Jass, Charles City, IA (US)

(73) Assignee: Cambrex Charles City, Inc., Charles City, IA (US)

( * ) Notice: Subject to any disclaimer, the term of this patent is extended or adjusted under 35 U.S.C. 154(b) by 0 days.

(21) Appl. No.: 11/492,731

(22) Filed: Jul. 25, 2006

(65) Prior Publication Data
US 2006/0258881 A1 Nov. 16, 2006

Related U.S. Application Data

(62) Division of application No. 11/069,165, filed on Feb. 26, 2005, now abandoned.

(51) Int. Cl.
*C07D 261/00* (2006.01)
*C07D 269/00* (2006.01)
*C07D 271/00* (2006.01)

(52) U.S. Cl. .................................... 560/135
(58) Field of Classification Search ............. 560/135
See application file for complete search history.

(56) References Cited

U.S. PATENT DOCUMENTS 5,051,533 A 9/1991 Verkade
5,780,769 A 7/1998 Russell et al.
6,852,878 B2 * 2/2005 Meng et al. ................ 562/42

OTHER PUBLICATIONS

Verkade et al "Recent Applications of Proazaphosphatranes in Organic Synthesis" Aldrichimica Acta, vol. 37, No. 1, 1,3-13, 2004.

* cited by examiner

*Primary Examiner*—Margaret D. Seaman
*Assistant Examiner*—Niloofar Rahmani
(74) *Attorney, Agent, or Firm*—Richard J. Hammond

(57) ABSTRACT

A method is described for the preparation of polymorphic forms of water-soluble derivatives of probucol compounds having the following formula

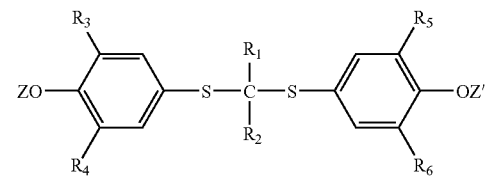

where $R_1$, $R_2$, $R_3$, $R_4$, $R_5$, $R_6$, Z and Z' are defined herein.

6 Claims, No Drawings

PROCESS FOR THE PREPARATION OF PROBUCOL DERIVATIVES

RELATIONSHIP TO PRIOR APPLICATIONS

This application is a division of application Ser. No. 11/069,165 filed as Feb. 26, 2005. This application is now abandoned.

FIELD OF INVENTION

The present invention relates to 4,4'-(isopropylidenedithio) bis[2,6-di-tert-butylphenol], known and referred to herein by its generic name "probucol", and to derivatives of probucol. More particularly, this invention relates to an improved process for the preparation of probucol derivatives

BACKGROUND OF THE INVENTION

Probucol is a well-known antioxidant that is related to antioxidant compounds such as 2-(3)-tertiary butyl-4-hydroxyanisole, 2,6-di-tertiary butyl-4-methylphenol and the like. These compounds are used in food and food products to prevent oxidative deterioration.

Probucol is represented by the following structural formula

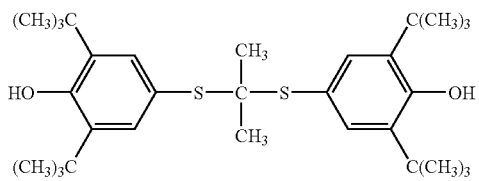

The preparation of this compound is a multistep process, typically starting by reacting a solution of the appropriately-substituted 4-mercaptophenol with acetone, in the presence of a catalytic amount of a strong acid. Probucol precipitates from the reaction mixture and is readily separated and purified. The reaction is described in detail in U.S. Pat. No. 3,862,332 (Barhhart et al).

Similarly, probucol and certain of its derivatives are also described in U.S. Pat. No. 3,485,843 (Wang), U.S. Pat. No. 3,576,833 (Neuworth) and U.S. Pat. No. 4,985,465 (Handler).

Probucol and its derivatives possess pharmaceutical properties that include antiatherogenesis, lipid lowering and the like. But probucol and numerous of its derivatives are poorly soluble in body fluids.

In order to avoid the low water solubility problems associated with probucol utilization in the body, more water-soluble derivatives have been prepared. Thus, U.S. Pat. No. 5,262,439 (Parthasarathy) discloses a class of water-soluble probucol derivatives having one or more ester groups replacing the phenolic hydroxyl group of the probucol molecule. Some of the compounds disclosed in this reference have polar or charged functionalities attached to the ester group, e.g., the groups carboxylic acid, amide, amino, and aldehyde. The method disclosed for preparing these water-soluble probucol compounds involves the reaction of probucol with the carboxylic acid anhydride compound bearing the desired polar or charged functionality in the presence of a catalyst.

Similarly, U.S. Pat. No. 6,323,359 also discloses water soluble derivatives of probucol. The compounds set forth in this patent are produced by a process involving the reaction of a probucol or the probucol compound with a base, such as an alkali metal or ammonium hydroxide or alkoxide to form a mono or dianion salt. The salt is then reacted with a carboxylic acid anhydrides to produce the desired water soluble derivative of probucol or probucol compound. See also U.S. Pat. No. 6,548,699.

Recently, the preparation of use of certain phosphorous-containing strong bases has been reported. See, for example, U.S. Pat. No. 5,051,533. These compounds, termed prophosphatranes, have the following formula:

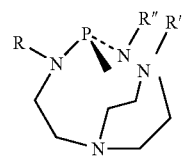

wherein R, R' and R" are hydrogen or $C_1$ to $C_8$ alkyl.

The prophosphatranes are bicyclic, nonionic bases in which the phosphorous atom functions as the site of electron pair donation. Since the conjugate acid of these compounds have a very high $pK_a$ value, the use of prophosphatranes in reactions that have been previously reserved for ionic bases such as sodium hydride, potassium tert-butoxide, etc. have proved fruitful. Thus, prophosphatrane compounds have been shown to be effective in reactions such as dehydrohalogenation, nitroaldol and alcohol silylation. Recently, in the presence of stoichiometric amounts of the prophosphatrane where R and R' in the above formula are methyl, acetic anhydride (as well as benzoic anhydride) has been shown to react with acid-labile or sterically hindered alcohols to produce acylated alcohols in good yield. See D'Sa et al, J. Org. Chem., 1996, 61, 2963.

The prior art processes used to produce water soluble derivatives of probucol or probucol compounds are disadvantageous, since they are not effective in producing the desired derivatives in any appreciable yields.

The use of prophosphatranes in the preparation of water soluble derivatives of probucol or probucol compounds has not been suggested.

Accordingly, it is desirable to have available a process to efficiently prepare probucol derivatives in high yields.

SUMMARY OF THE INVENTION

The present invention is a process to produce water soluble derivatives of probucol or probucol compounds. The process comprises the reaction of a solution of probucol or a probucol compound with a carboxylic acid anhydride such as succinic acid anhydride, glutaric acid anhydride, adipic acid anhydride, suberic acid anhydride, sebacic acid anhydride, azelaic acid anhydride, phthalic acid anhydride or maleic acid anhydride and a prophosphatrane compound of the formula

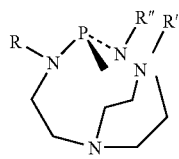

wherein R, R' and R" are the same or different and are hydrogen or $C_1$ to $C_8$ alkyl. From this reaction, a reaction mixture is produced that contains the water soluble derivative of probucol or a probucol compound. These water soluble derivative of probucol or the probucol compound can then be separated from the reaction mixture.

DESCRIPTION OF THE PREFERRED EMBODIMENTS

The present invention provides an improved process for preparing certain water soluble derivatives of probucol or probucol compounds.

As used herein, the term "$C_1$ to $C_8$ alkyl" is intended to mean and include the groups that are $C_1$ to $C_8$ linear or branched alkyl which include the moieties methyl, ethyl, n-propyl, isopropyl, isobutyl, sec-butyl, tert-butyl, n-pentyl, 2-methylpentyl, n-heptyl, n-octyl and the like.

The term "$C_6$ to $C_{12}$ aryl" is intended to mean and include the aromatic radicals having 6 to 12 carbon atoms in the aromatic ring system that may be substituted or unsubstituted one or more times by alkyl, nitro or halo which includes phenyl, naphthyl, phenanthryl, anthracenyl, thienyl, pyrazolyl and the like.

The term "$C_3$ to $C_6$ alkenyl" is intended to mean and include the groups that are $C_3$ to $C_6$ linear or branched alkenyl which include the moieties 1-propenyl, 1-butenyl, 2-butenyl, 1-pentenyl, 2-pentenyl and the like.

The water-soluble derivatives of probucol or the probucol compounds herein are obtained by reaction of one or both of the hydroxyl groups of probucol or the probucol compound with a prophosphatrane compound that abstracts at least one proton from the hydroxyl group of probucol or the probucol compound. The ionized probucol or probucol compound that is produced from such proton abstraction then attacks the carboxyl moiety of the anhydride group, forming an ester with a carboxylic acid terminal group.

The prophosphatrane compound used in the above described reaction has the formula

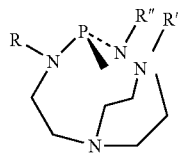

where R, R' and R" are the same or different and are hydrogen or $C_1$ to $C_8$ alkyl.

It is preferred that R, R' and R" are the same or different and are hydrogen or $C_1$ to $C_4$ alkyl, most preferably the same and are methyl or isobutyl.

The reaction of probucol or a probucol compound with the prophosphatrane compound is preferably carried out in an organic solvent for a time and at a temperature sufficient to form the ionized probucol or probucol compound and allow such anionic moiety to then attack the anhydride to produce the water soluble derivative of probucol or the probucol compound. Proper selection of the organic solvent produces a reaction solution in which the prophosphatrane reactant precipitates from the reaction solution and is subsequently readily removed. Suitable solvents include chlorinated hydrocarbons, ketones, aromatic hydrocarbons and ethers. Preferably the solvent is ketone such as acetone.

The temperature of the reaction can be room temperature or it can be higher, e.g., up to about 100° C. The reaction is carried out for about 30 minutes to about 2 hours. Preferably the reaction is carried out for about 60 minutes to about 90 minutes at 25° to about 30° C.

It should be noted that because there are two reactive sites available in the mono- and dianionic mixture, either one or both of these sites can be substituted by the incoming acid anhydride moiety.

The reaction of the anionic probucol or probucol compound with an acid anhydride such as succinic acid anhydride, glutaric acid anhydride, adipic acid anhydride, suberic acid anhydride, sebacic acid anhydride, azelaic acid anhydride, phthalic acid anhydride or maleic acid anhydride produces the compounds of the formula below

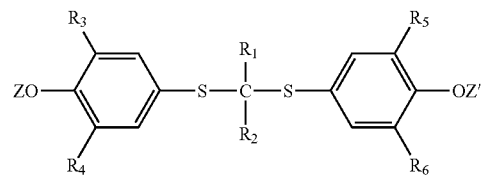

where $R_1$ and $R_2$ are the same or different and are alkyl, alkenyl or aryl having from 1 to 8 carbon atoms and $R_3$, $R_4$, $R_5$ and $R_6$ are the same or different and are alkyl having from 1 to 4 carbon atoms, Z and Z' are the same or different and are hydrogen, or the moiety —C(O)—$C_1$ to $C_6$ alkyl C(O)OH or the moiety —C(O)—$C_3$ to $C_6$— alkenyl C(O)OH with the proviso that Z and Z' can not both be hydrogen.

Preferably, $R_1$ and $R_2$ are the same and are alkyl having from 1 to 6 carbon atoms, most preferably methyl.

Preferably $R_3$, $R_4$, $R_5$ and $R_6$ are the same and are alkyl having from 1 to 4 carbon atoms, most preferably tert-butyl As noted, two probucol derivatives may be formed, i.e., the desired mono substitution product, where Z and Z' are different and are hydrogen and the moiety —C(O)—$C_1$ to $C_6$-alkyl C(O)OH or the moiety —C(O)—$C_3$ to $C_6$ alkenyl-C(O)OH where alkyl, and alkenyl are as previously defined or the disubstitution product, where Z and Z' are the same and are the moiety —C(O)—$C_1$ to $C_6$-alkyl C(O)OH or the moiety —C(O)—$C_3$ to $C_6$ alkenyl-C(O)OH where alkyl, and alkenyl are as previously defined.

The separation of these compounds is typically accomplished by using a solvent that selectively dissolves one of the products but not the other. Organic hydrocarbon solvents having the formulas $C_n$ to $H_{2n+2}$ where n is an integer from 5 to 10 have been found useful in demonstrating such selectivity.

Typically, the organic solvent used to carry out the reaction is removed, usually by distillation, an aqueous solution of an alkali or alkaline earth metal hydroxide is added and the resulting residue extracted with the organic aliphatic hydrocarbon at a high pH. The water soluble derivatives or probucol or the probucol compound selectively dissolve. It should be noted that the solubility of the derivatives of probucol or the probucol compound are dependent on temperature and pH.

After separation of the organic and aqueous phases, the desired mono substitution product, i.e., where Z and Z' are different and are hydrogen and the moiety —C(O)—$C_1$ to $C_6$-alkyl C(O)OH or the moiety —C(O)—$C_3$ to $C_6$ alkenyl-C(O)OH where alkyl, and alkenyl are as previously defined, is obtained from the organic phase and recovered by evaporation of the solvent or by cooling of the solution.

It is preferred that the integer n of the hydrocarbon solvent is 6 to 9, Most preferably the hydrocarbon solvent is hexane, heptane or octane.

EXAMPLES

Synthesis of Water Soluble Derivatives of Probucol

Example 1

To a 20 mL reactor equipped with magnetic stiring was charges probucol (517 mg., 1 mmol) and acetone (2 mL). To the resulting clear solution was charged succinic anhydride (100 mg, 1 mmol). To the new, nearly colorless solution was added 2,8,9-triisobutyl-2,5,8,9-tetraaza-1-phosphabicyclo[3.3.3]undecane (iBuVSB, 330 mg, 1 mmol). Addition of the base provided an exotherm and a deep purple solution. HPLC analysis at the time intervals shown below gave the following area percent ratios (DSP is the disuccinyl ester of probucol, MSP is the monosuccinyl ester of probucol, and PRO is probucol): HPLC after:

10 minutes at ambient temperature, 0.95 DSP, 15.0 MSP, 84.1 PRO;

30 minutes at ambient temperature, unchanged; and 48 hours at ambient temperature, 0.34 DSP, 11.3 MSP, 88.4 PRO.

Example 2

To a 10 mL reactor equipped with magnetic stirring was charged probucol (260 mg, 0.5 mmol) and toluene (1 mL). To the resulting clear solution was charged succinic anhydride (50 mg, 0.5 mmol). The newly formed slurry was sonicated at 25° C. to give a thin slurry. To this slurry was added iBuVSB (165 mg, 0.5 mmol). Addition of the base provided an exotherm and a deep purple solution. HPLC analysis at the time intervals shown below gave the following area percent ratios (DSP is the disuccinyl ester of probucol, MSP is the monosuccinyl ester of probucol, and PRO is probucol): HPLC after:

1.5 hours at ambient temperature, 11.6 DSP, 42.1 MSP, 46.2 PRO; and 14 hours at ambient temperature, 7.64 DSP, 39.3 MSP, 52.9 PRO.

I claim:

1. A process for the preparation of a water-soluble derivative of probucol having the following formula

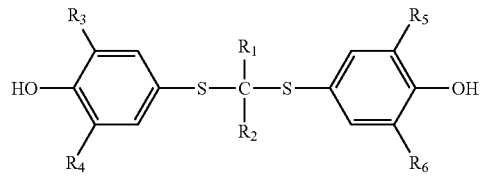

where $R_1$ and $R_2$ are the same or different and are -$C_1$-$C_6$ alkyl, -$C_3$-$C_6$ alkenyl or aryl, $R_3$, $R_4$, $R_5$ and $R_6$ are the same or different and are $C_1$-$C_6$ alkyl, Z and Z' are the same or different and are hydrogen or the groups that are saturated acyl or unsaturated acyl having from 1 to 8 carbon atoms said saturated acyl or unsaturated acyl containing a polar or charged functionality where Z and Z' can not both be hydrogen by mixing a probucol compound of the formula

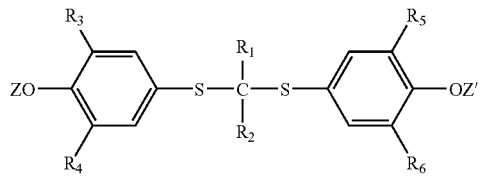

where $R_1$, $R_2$, $R_3$, $R_4$, $R_5$ and $R_6$ are as previously defined with a carboxylic acid anhydride selected from the group consisting of succinic acid anhydride, glutaric acid anhydride, adipic acid anhydride, suberic acid anhydride, sebacic acid anhydride, azelaic acid anhydride, phthalic acid anhydride or maleic acid anhydride and a prophosphatrane compound of the formula

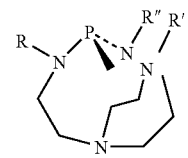

where R, R' and R" are the same or different and are hydrogen or $C_1$ to $C_8$ alkyl to form a reaction mixture and then separating the water soluble derivative of probucol or the probucol compound from said reaction mixture.

2. A process for the preparation of a water-soluble derivative of probucol having the following formula

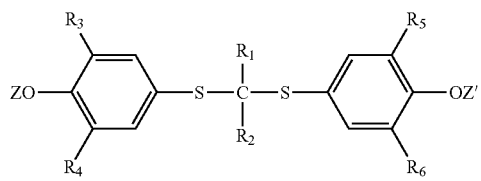

where $R_1$ and $R_2$ are the same or different and are —$C_1$-$C_6$ alkyl, —$C_3$-$C_6$ alkenyl or aryl, $R_3$, $R_4$, $R_5$ and $R_6$ are the same or different and are $C_1$-$C_6$ alkyl, Z and Z' are the same or different and are hydrogen or the groups that are saturated acyl or unsaturated acyl having from 1 to 8 carbon atoms said saturated acyl or unsaturated acyl containing a polar or charged functionality where Z and Z' can not both be hydrogen by mixing a probucol compound of the formula

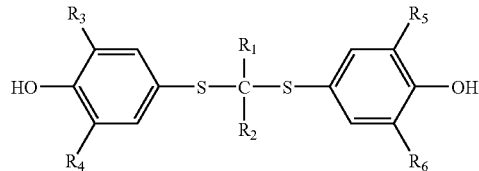

where $R_1$, $R_2$, $R_3$, $R_4$, $R_5$ and $R_6$ are as previously defined with a carboxylic acid anhydride selected from the group consisting of succinic acid anhydride, glutaric acid anhydride, adipic acid anhydride, suberic acid anhydride, sebacic acid anhydride, azelaic acid anhydride, phthalic acid anhydride or maleic acid anhydride and a prophosphatrane compound of the formula

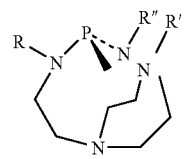

where R, R' and R" are the same or different and are hydrogen or $C_1$ to $C_8$ alkyl to form a reaction mixture and then separating the water soluble derivative of probucol or the probucol compound from said reaction mixture.

3. The process according to claim 2 wherein R, R' and R" are the same or different and are hydrogen or $C_1$ to $C_4$ alkyl.

4. The process according to claim 3 wherein R, R' and R" are the same and are methyl or isobutyl.

5. The process according to claim 2 wherein the reaction is carried out over a period of from about 30 minutes to about 2 hours at about 25° to about 100° C.

6. The process according to claim 5 wherein the reaction is carried out over a period of from about 60 minutes to about 90 minutes at about 25° to about 30° C.

* * * * *